United States Patent
Schafer et al.

[11] Patent Number: 6,143,032
[45] Date of Patent: Nov. 7, 2000

[54] INTERVERTEBRAL IMPLANT

[75] Inventors: Bernd Schafer, Goppingen; Henry Halm, Bissendorf-Wissingen, both of Germany

[73] Assignee: Schafer micomed GmbH, Goppingen, Germany

[21] Appl. No.: 09/190,151

[22] Filed: Nov. 12, 1998

[30] Foreign Application Priority Data

Nov. 12, 1997 [DE]  Germany ................. 297 20 022 U

[51] Int. Cl.⁷ ..................................................... A61F 2/44
[52] U.S. Cl. ................................. 623/17.11; 606/61
[58] Field of Search ..................... 623/16, 17, 18, 623/16.11, 17.11–17.16, 18.11; 606/60, 61

[56] References Cited

U.S. PATENT DOCUMENTS

| | | | |
|---|---|---|---|
| 5,171,281 | 12/1992 | Parsons et al. | 623/17.15 |
| 5,192,327 | 3/1993 | Brantigan | 623/17 |
| 5,306,309 | 4/1994 | Wagner et al. | 623/17 |
| 5,344,459 | 9/1994 | Swartz | 623/18.11 |
| 5,425,772 | 6/1995 | Brantigan | 623/17 |
| 5,609,637 | 3/1997 | Biedermann et al. | 623/17 |
| 5,702,449 | 12/1997 | McKay | 623/17 |
| 5,702,451 | 12/1997 | Biedermann et al. | 623/17 |
| 5,766,252 | 6/1998 | Henry et al. | 623/17 |
| 5,860,973 | 1/1999 | Michelson | 623/17 |
| 5,861,041 | 1/1999 | Tienboon | 623/17.16 |
| 5,865,845 | 2/1999 | Thalgott | 623/17 |
| 5,888,222 | 3/1999 | Coates et al. | 623/17 |
| 5,888,224 | 3/1999 | Beckers et al. | 623/17 |
| 5,897,556 | 4/1999 | Drewry et al. | 623/17 |

FOREIGN PATENT DOCUMENTS

| | | | |
|---|---|---|---|
| 97/06753 | 2/1997 | WIPO | 623/17.11 |
| 97/15247 | 5/1997 | WIPO | 623/17.11 |

*Primary Examiner*—V. Millin
*Assistant Examiner*—Tram A. Nguyen
*Attorney, Agent, or Firm*—Jones, Tullar & Cooper, P.C.

[57] ABSTRACT

The present invention relates to an intervertebral implant for insertion between two vertebral bodies of a spinal column, comprising a body containing two contact faces, whereby the body is designed as a hollow body, and the hollow body is formed by a side wall which has a convexly curved longitudinal wall portion and a concavely curved longitudinal wall portion as well as two convexly curved lateral wall portions connecting the two longitudinal wall portions with each other, whereby the radii of curvature of the lateral wall portions are smaller than the radii of curvature of the longitudinal wall portions.

14 Claims, 1 Drawing Sheet

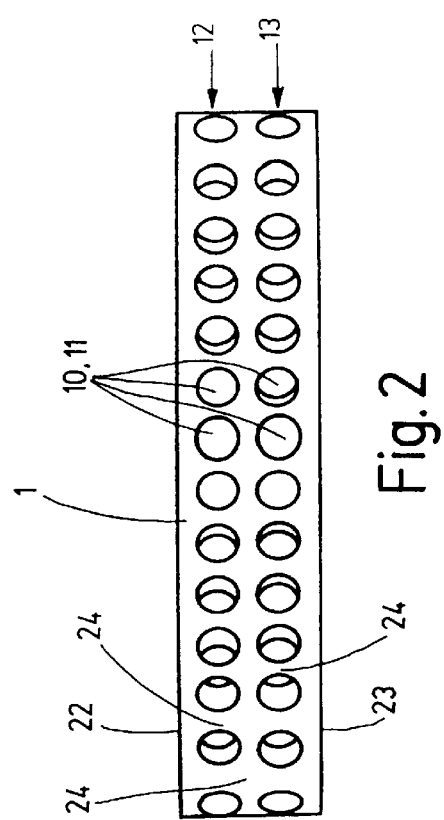
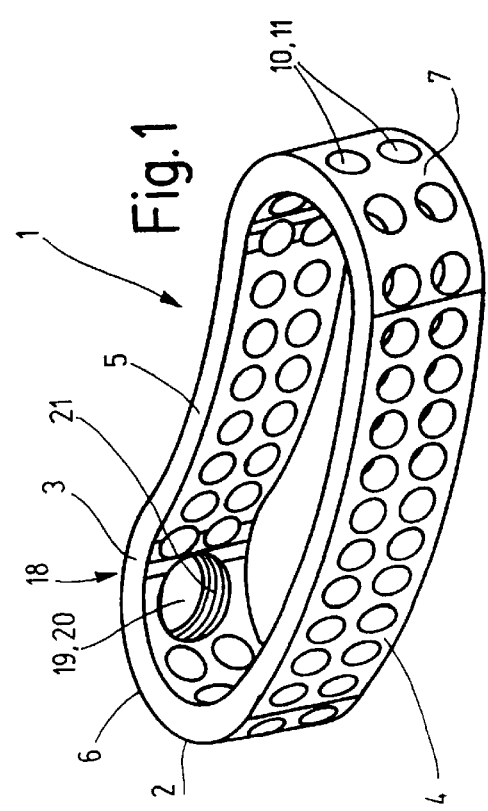
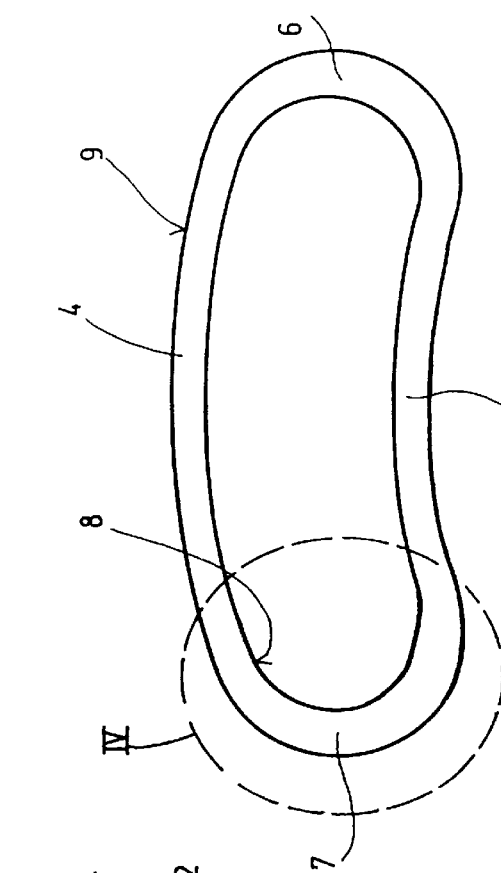
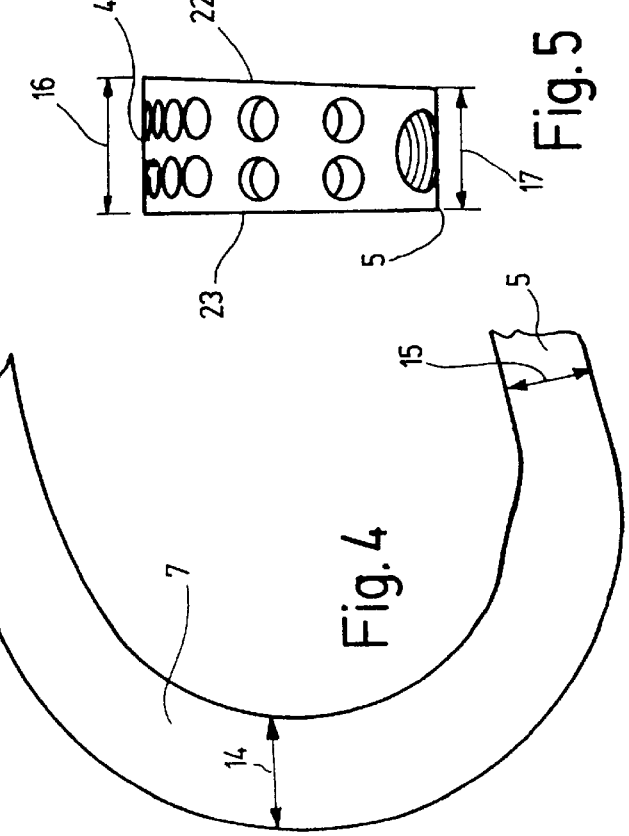

INTERVERTEBRAL IMPLANT

FIELD OF THE INVENTION

The present invention relates to an intervertebral implant for insertion between two vertebral bodies of a spinal column, comprising a body containing two contact faces.

BACKGROUND OF THE INVENTION

Among the components of each individual vertebra of the spinal column are a vertebral body, a vertebral arch, a spinal process, two transverse processes, and two superior and two inferior articular processes. The vertebrae are connected with each other by intervertebral discs (disci intervertebralis) which contact their vertebral bodies (corpus vertebrae). These intervertebral discs, which consist of fibro-cartilage that is rich in fluid, connect the individual vertebrae with each other. The size of the intervertebral discs increases from the top of the spine to the bottom, in accordance with the stresses occurring m the human body. The intervertebral discs serve as elastic shock absorbers and provide cushions against impact. It is known that the intervertebral discs can be displaced, or that the inner gelatinous core (nucleus pulposus) may prolapse through cracks in the connective tissue-like cartilaginous outer ring (annulus fibrosus). The intervertebral disc may partly enter the intervertebral foramina (foramina intervertebralis) or the spinal canal. This prolapse can also be medial, dorsally medial or lateraL Such types of prolapse occur mostly at vertebrae $L_4$–$L_5$, $L_6$-$_s$1 and $C_6$–$C_7$. If such types of prolapse are not treated, they result in irreversible compression of the nerve roots or in transverse lesions. If symptomatic physiotherapy, such as exercises or message, promise no success, the discus intervertebralis must be surgically removed. Now there is a possibility of implanting an artificial intervertebral disc or performing osteosynthesis of the two vertebrae via a rigid intervertebral implant.

From EP 392 076 A1, an artificial intervertebral disc is known which consists of a superior and an inferior contact face (called upper and lower flat rigid plates in the European patent) and an elastic intermediate layer (called flat elastomeric core in the European patent). Protruding from the contact face are anchor bolts (called protuberances in the European patent) by which the intervertebral disc is fixed to the vertebral bodies. It has proven a disadvantage that due to the elastic intermediate layer between the two contact faces no optimal synthesis of the two vertebrae can be achieved.

From U.S. Pat. No. 5,192,327, a rigid intervertebral implant is known which is also inserted between two vertebral bodies for osteosynthesis. In this implant, the two vertebrae must be placed at a predetermined distance from each other before the implant can be inserted. If the distance between the two vertebrae is too great, the implant can easily slip, or it may not have a firm hold.

Both of these intervertebral implants have the disadvantage that the operation for inserting these implants must be ventral. This is not only time-consuming and costly, but also very stressful for the patient, since there is certainly a possibility that the spinal column is stabilized on the posterior side while a ventral intervention is still necessary to insert the intervertebral implant.

SUMMARY OF THE INVENTION

An object of the present invention is to provide an intervertebral implant which can be inserted between two vertebral bodies of a spinal column by means of a dorsal intervention.

This object is achieved by having the body of the intervertebral implant designed as a hollow body. The hollow body is formed by a side wall which has a convexly curved longitudinal wall portion and a concavely curved longitudinal wall portion as well as two convexly curved lateral wall portions connecting the two longitudinal wall portions with each other, whereby the radii of curvature of the two lateral wall portions are smaller than the radii of curvature of the two longitudinal wall portions.

When an intervertebral implant according to the present invention is designed in that manner, the substantial advantage is created that with a dorsal intervention, this intervertebral implant can be inserted into the body ventrally between the two vertebral bodies. Prior to this, the two vertebral bodies were stabilized from the dorsal side by means of bone screws and appropriate fixing means, and a large enough distance was created between the two vertebral bodies to allow the insertion of the intervertebral implant. When the implant assumes its correct position, the two vertebral bodies are compressed and fixed, which holds the intervertebral implant in place. This process can be performed exclusively by a posterior surgical intervention, which means considerably less stress for the patient and also poses a smaller risk than an intervention from the dorsal as well as from the ventral side.

In a preferred embodiment, the side wall of the hollow body is curved in kidney-shaped fashion, whereby the two longitudinal wall portions both have the same radius of curvature. However, it is also conceivable to have intervertebral implants in which the convexly curved longitudinal wall portion has a greater radius of curvature than the concavely curved longitudinal wall portion.

Advantageously, the side wall is provided with openings. This design has the substantial advantage that it is relatively simple and light in weight and that it allows bone tissue to grow easily through the openings. Advantageously, the openings are formed by drilling holes. The side wall is provided with two rows of openings which are positioned symmetrically to each other. Although there is little material required, the result is a stable structure which can support even great forces.

Advantageously, the lateral wall portions and/or longitudinal wall portions are curved in the form of a circular arc, so that the intervertebral implant can best match the shape of the vertebral bodies.

According to a preferred embodiment, at least one lateral wall portion is thicker than the longitudinal wall portions. The lateral wall portion which is thicker is provided with an instrument receptacle formed by a hole with an inside thread. Into this hole, an instrument can be screwed with which the intervertebral implant can be inserted dorsally into the body and from the ventral side placed between the two vertebral bodies. As soon as the intervertebral implant assumes its correct position, the instrument is detached from the instrument receptacle and removed from the body. Now, the intervertebral implant can be fixed.

Advantageously, the instrument receptacle is situated in an intermediate area between a longitudinal wall portion and a lateral wall portion. This intermediate area between the lateral wall portion and the longitudinal wall portion has the substantial advantage that the instrument, which extends outwardly from the intervertebral implant, allows the correct insertion of the intervertebral implant into the desired position between the two vertebral bodies without the instrument colliding with parts of the spinal column.

The intermediate area containing the instrument receptacle is situated where the concavely curved longitudinal wall portion turns into the convexly curved lateral wall portion, whereby the instrument receptacle lies in the lateral wall portion.

The intervertebral implant has a wedge-shaped form, so that the two contact faces lie in planes that are at an angle to each other. In this manner, the position of the two vertebral bodies to be fixed against each other is substantially maintained. Preferably, the height of the concavely curved longitudinal wall portion is smaller than the height of the convexly curved wall portion. For example, the difference in height between these two walls may be 1 mm Advantageously, the concavely curved longitudinal wall portion of the intervertebral implant according to the present invention lies on the dorsal side. The intervertebral implant is made of metal and/or plastic and/or ceramic so that it can be sterilized.

Other advantages, characteristics and details of the present invention are indicated by means of the following description in which, with reference to the drawings, one preferred embodiment is described. The characteristics mentioned in the description and shown in the drawings can be essential for the present invention alone or in any combination.

BRIEF DESCRIPTION OF THE DRAWINGS

FIG. 1 is a perspective view of a preferred embodiment of the intervertebral implant according to the present invention;

FIG. 2 is a lateral view of the intervertebral implant shown in FIG. 1;

FIG. 3 is a top view of the intervertebral implant;

FIG. 4 is an enlarged view IV of the left lateral portion wall of the intervertebral implant as shown in FIG. 3; and FIG. 5 is a lateral view of the lateral wall portion of the intervertebral implant.

DESCRIPTION OF THE PREFERRED EMBODIMENTS

FIG. 1 shows a perspective view of the intervertebral implant 1 in accordance with the present invention. The intervertebral implant 1 is designed as a hollow body 2 which is formed by a side wall 3. This side wall 3 consists of two longitudinal wall portions 4 and 5 and two lateral wall portions 6 and 7. The longitudinal wall portions 4 and 5 and the lateral wall portions 6 and 7 merge in such a way that they take a joint shape. The longitudinal wall portion 4 is convexly curved, and the longitudinal wall portion 5 is concavely curved. Furthermore, the lateral wall portions 6 and 7 are convexly curved.

As FIG. 3 clearly shows, the radii of curvature of the lateral wall portions 6 and 7 are smaller than the radii of curvature of longitudinal wall portions 4 and 5. For example, the radius of curvature on the inside 8 of the lateral wall portions 6 and 7 is 4.6 mm. Furthermore, the radius of curvature of the outside 9 of longitudinal wall portion 4, is about 50 mm, which is greater than the radius of curvature of the outside 9 of longitudinal wall portion 5, at about 35 mm. Also, FIGS. 1 and 3 clearly show that intervertebral implant 1 is approximately kidney-shaped.

Side wall 3 is provided with holes 11 forming openings 10 arranged in two rows 12 and 13 (FIG. 2). Furthermore, the arrangement of the holes 11 in rows 12 and 13 is symmetrical, re., over each bottom hole 11, a top hole 11 can be recognized. Thus, the two contact faces 22 and 23 support each other directly via webs 24.

FIG. 4 clearly shows that the wall thickness 14 of the lateral wall portion 7 is greater than the wall thickness 15 of the longitudinal wall portion 5. Furthermore, the wall thickness 14 of the lateral wall portion 7 is greater than the wall thickness of longitudinal wall portion 4. Moreover, additionally or alternatively, the wall thickness of the lateral wall portion 6 can be greater than the wall thicknesses of the two longitudinal wall portions 4 and 5.

FIG. 5 clearly shows that height 16 of the convexly curved longitudinal wall portion 4 is greater than height 17 of the concavely curved longitudinal wall portion 5. As a result, the intervertebral implant 1 is wedge-shaped, so that the planes of the two contact faces 22 and 23 intersect.

FIGS. 1 and 5 also show that in the intermediate area 18 between lateral wall portion 6 and convexly curved longitudinal wall portion 5, a hole 20 forming an instrument receptacle 19 is provided in side wall 3, in particular in lateral wall portion 6. This hole 20 is designed as a threaded hole provided with an internal thread 21. To this instrument receptacle 19, an instrument for inserting and placing the intervertebral implant 1 can be connected.

Since the threaded hole 20 is arranged in an area of side wall 3 which has a greater wall thickness 14, namely in lateral wall portion 6, there is no risk of damaging the internal thread 21 when applying the instrument or inserting the intervertebral implant 1 into the patient's body.

During a posterior intervention, such an intervertebral implant 1 can be inserted without a problem dorsally into the body, and it can be inserted ventrally between the two vertebral bodies.

What is claimed is:

1. An intervertebral implant for insertion between two vertebral bodies of a spinal column comprising a hollow body formed by a side wall, the spinal column having a dorsal side, said intervertebral implant having:

a convexly curved longitudinal wall portion;

a concavely curved longitudinal wall portion; and two convexly curved lateral wall portions connecting said convexly curved longitudinal wall portion and said concavely curved longitudinal wall portion, whereby the radii of curvature of said two convex curved lateral wall portions are smaller than the radii of curvature of said convexly curved longitudinal wall portion and said concavely curved longitudinal wall portion, and whereby said wall portions define two contact surfaces; whereby:

the wall thickness of at least one of said two convexly curved lateral wall portions is greater than the wall thickness of said convex curved longitudinal wall portion and said concavely curved longitudinal wall portion;

one of said two convexly curved lateral wall portions is provided with an instrument receptacle; and said instrument receptacle is formed as a hole provided with an internal thread.

2. The intervertebral implant as defined in claim 1, whereby said convexly curved longitudinal wall portion, said concavely curved longitudinal wall portion and said two convexly curved lateral wall portions together have a kidney-shaped form.

3. The intervertebral implant as defined in claim 1, whereby said convexly curved longitudinal wall portion and said concavely curved longitudinal wall portion have the same radius of curvature.

4. The intervertebral implant as defined in claim 1, whereby said hollow body is provided with openings through said wall portions.

5. The intervertebral implant as defined in claim 4, whereby said openings are formed by holes.

6. The intervertebral implant as defined in claim 4, whereby said hollow body is provided with two rows of openings.

7. The intervertebral implant as defined in claim 6, whereby said two rows of openings are arranged symmetrical to each other.

8. The intervertebral implant as defined in claim 1, whereby said convexly curved longitudinal wall portion and said concavely curved longitudinal wall portion are curved in the form of a circular arc.

9. The intervertebral implant as defined in claim 1, whereby said instrument receptacle is situated in an intermediate area between a curved longitudinal wall portion and a curved lateral wall portion.

10. The intervertebral implant as defined in claim 9, whereby curved longitudinal wall portion is concavely curved.

11. The intervertebral implant as defined in claim 1, whereby said contact surfaces lie in planes that are situated at an angle to each other.

12. The intervertebral implant as defined in claim 1, whereby the height of said concavely curved longitudinal wall portion is smaller than the height of said convexly curved longitudinal wall portion.

13. The intervertebral implant as defined in claim 1, whereby said concavely curved longitudinal wall portion lies on the dorsal side of the spinal column.

14. The intervertebral implant as defined in claim 1, whereby said hollow consists of one of: metal, plastic, metal and plastic, metal and ceramic, and ceramic.

* * * * *